United States Patent
Martin et al.

(10) Patent No.: US 9,457,127 B2
(45) Date of Patent: Oct. 4, 2016

(54) MICRO-FIBER WEBS OF POLY-4-HYDROXYBUTYRATE AND COPOLYMERS THEREOF PRODUCED BY CENTRIFUGAL SPINNING

(71) Applicant: Tepha, Inc., Lexington, MA (US)

(72) Inventors: David P. Martin, Arlington, MA (US); Said Rizk, Windham, NH (US)

(73) Assignee: Tepha, Inc., Lexington, MA (US)

( * ) Notice: Subject to any disclaimer, the term of this patent is extended or adjusted under 35 U.S.C. 154(b) by 0 days.

(21) Appl. No.: 14/661,172

(22) Filed: Mar. 18, 2015

(65) Prior Publication Data

US 2015/0265746 A1    Sep. 24, 2015

Related U.S. Application Data

(60) Provisional application No. 61/955,080, filed on Mar. 18, 2014.

(51) Int. Cl.

| | | |
|---|---|---|
| A61L 27/18 | (2006.01) |
| A61F 2/02 | (2006.01) |
| A61L 15/44 | (2006.01) |
| A61L 27/54 | (2006.01) |
| A61L 27/60 | (2006.01) |
| A61L 31/06 | (2006.01) |
| A61F 13/00 | (2006.01) |
| A61L 15/26 | (2006.01) |
| A61L 27/36 | (2006.01) |
| C08K 3/00 | (2006.01) |
| C08K 5/00 | (2006.01) |
| D01F 6/62 | (2006.01) |
| D04H 1/435 | (2012.01) |
| D01D 5/18 | (2006.01) |
| D04H 1/72 | (2012.01) |
| A61L 27/26 | (2006.01) |
| A61L 27/50 | (2006.01) |
| A61L 31/04 | (2006.01) |
| A61L 31/14 | (2006.01) |
| A61L 15/22 | (2006.01) |
| A61L 15/42 | (2006.01) |

(52) U.S. Cl.
CPC ............... *A61L 27/18* (2013.01); *A61F 2/02* (2013.01); *A61F 13/00017* (2013.01); *A61F 13/00021* (2013.01); *A61L 15/225* (2013.01); *A61L 15/26* (2013.01); *A61L 15/42* (2013.01); *A61L 15/44* (2013.01); *A61L 27/26* (2013.01); *A61L 27/36* (2013.01); *A61L 27/50* (2013.01); *A61L 27/54* (2013.01); *A61L 27/60* (2013.01); *A61L 31/041* (2013.01); *A61L 31/06* (2013.01); *A61L 31/14* (2013.01); *C08K 3/0008* (2013.01); *C08K 5/0008* (2013.01); *D01D 5/18* (2013.01); *D01F 6/625* (2013.01); *D04H 1/435* (2013.01); *D04H 1/72* (2013.01); *A61L 2420/02* (2013.01)

(58) Field of Classification Search
CPC ....... A61L 27/18; A61L 31/06; A61L 29/06; A61L 15/26; A61L 27/34; A61L 17/12; A61L 2300/00; A61L 31/148; A61L 31/16; A61L 26/0019; A61L 31/10; A61L 27/58; A61L 17/10; A61L 27/54; A61L 29/16
See application file for complete search history.

(56) References Cited

U.S. PATENT DOCUMENTS

| | | |
|---|---|---|
| 4,603,070 A | 7/1986 | Steel |
| 5,811,272 A | 9/1998 | Snell |
| 6,316,262 B1 | 11/2001 | Huisman |
| 6,548,569 B1 | 4/2003 | Williams |
| 6,555,123 B2 | 4/2003 | Williams |
| 6,585,994 B2 | 7/2003 | Williams |
| 6,610,764 B1 | 8/2003 | Martin |
| 6,878,758 B2 | 4/2005 | Martin et al. |
| 6,905,987 B2 | 6/2005 | Noda |
| 7,025,980 B1 | 4/2006 | Williams |
| 7,553,923 B2 | 6/2009 | Williams |
| 7,618,448 B2 | 11/2009 | Schmitz |

(Continued)

FOREIGN PATENT DOCUMENTS

| | | |
|---|---|---|
| WO | 9523249 | 8/1995 |
| WO | 9932536 | 7/1999 |
| WO | 0056376 | 9/2000 |
| WO | 2011119742 | 9/2011 |
| WO | 2011159784 | 12/2011 |

OTHER PUBLICATIONS

Martin et al. "Medical applications of poly-4-hydroxybutyrate: a strong flexible absorbable biomaterial", Biochemical Engineering Journal 16, 97-105 (2003).*

(Continued)

*Primary Examiner* — Audrea Buckley
(74) *Attorney, Agent, or Firm* — Pabst Patent Group LLP

(57) ABSTRACT

Methods to produce micro-fiber webs containing fibers of 4-hydroxybutyrate or copolymers thereof with average diameters from 0.01 to 100 μm, have been developed. The micro-fiber webs are produced by centrifugal spinning. These methods allow the micro-fiber webs to be produced without substantial loss of the polymer weight average molecular weight. Webs containing micro-fibers of poly-4-hydroxybutyrate or copolymer thereof, are made by centrifugal spinning. The micro-fibers have average diameters ranging from 0.01 to 100 μm and contain crimped fibers with a higher elongation at break fibers when compared to fibers derived by melt-blown extrusion, dry spinning and electrospinning. The fibers of the micro-fiber webs have a high degree of orientation. These micro-fiber webs can be used for a variety of purposes including fabrication of medical devices.

19 Claims, 1 Drawing Sheet

(56) References Cited

U.S. PATENT DOCUMENTS

| | | | |
|---|---|---|---|
| 7,641,825 B2 | 1/2010 | Rizk | |
| 8,016,883 B2 | 9/2011 | Coleman | |
| 8,034,270 B2 | 10/2011 | Martin | |
| 8,039,237 B2 | 10/2011 | Martin | |
| 8,231,889 B2 | 7/2012 | Williams | |
| 8,287,909 B2 | 10/2012 | Martin | |
| 2009/0162276 A1 | 6/2009 | Martin | |
| 2012/0150285 A1* | 6/2012 | Cahil | A61L 27/18 623/1.46 |

OTHER PUBLICATIONS

Hori, et al., "Chemical synthesis of high molecular weight poly(3-hydroxybutyrate-co-4-hydroxybutyrate)", Polymer, 36:4703-5 (1995).

Houk, et al., "Why delta-valerolactone polymerizes and gamma-butyrolactone does not", J. Org. Chem., 73 (7), 2674-8 (2008).

Martin, et al., "Medical applications of poly-4-hydroxybutyrate: a strong flexible absorbable biomaterial", Biochem. Eng. J., 16:97-105 (2003).

Vaz, et al., Novel Electrospun P4HB:PCL Scaffold for Aortic Valve Tissue Engineering, Poster Presentation (2004), Eindhoven University of Technology.

Williams, et al., "Poly-4-hydroxybutyrate (P4HB): a new generation of resorbable medical devices for tissue repair and regeneration", Biomed. Tech. 58 (5):439-452 (2013).

Williams, et al., "Applications of PHA\s in medicine and pharmacy", Polyesters, III, 4:91-127 (2002).

International Search Report for PCT Application PCT/US2015/021176 mailed Jun. 25, 2015.

* cited by examiner

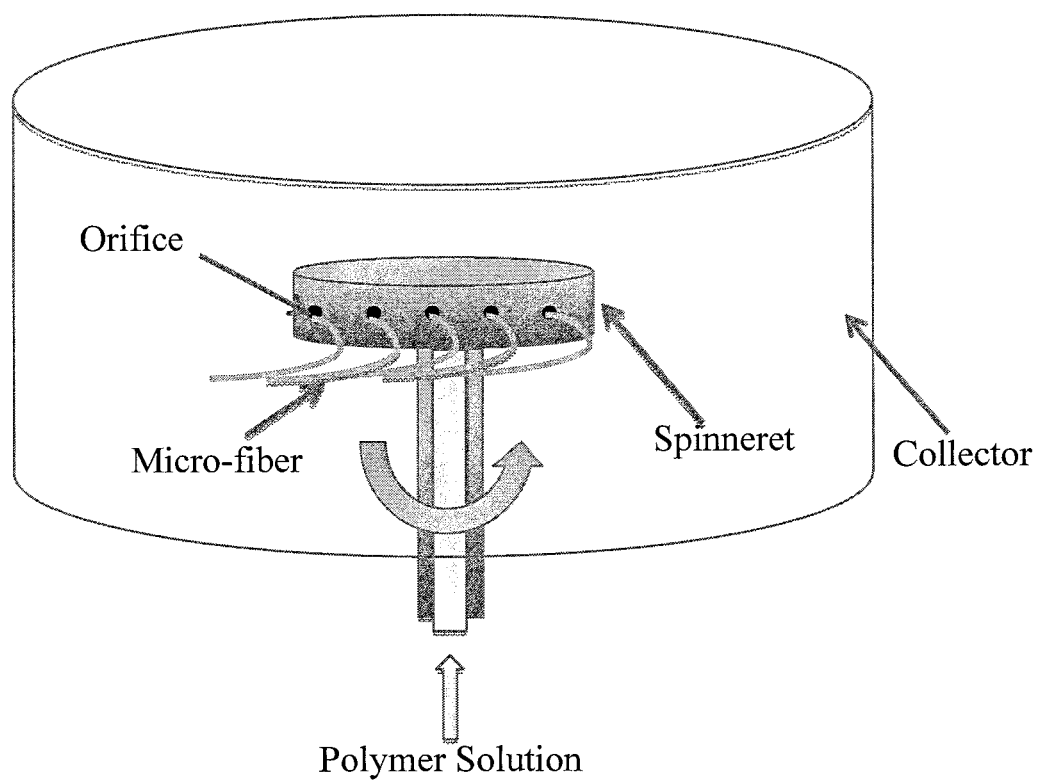

MICRO-FIBER WEBS OF POLY-4-HYDROXYBUTYRATE AND COPOLYMERS THEREOF PRODUCED BY CENTRIFUGAL SPINNING

CROSS-REFERENCE TO RELATED APPLICATIONS

This application claims priority to U.S. Ser. No. 61/955,080, filed on Mar. 18, 2014, which is incorporated herein in its entirety.

FIELD OF THE INVENTION

The present invention generally relates to micro-fiber webs containing fibers of poly-4-hydroxybutyrate (P4HB) and copolymers thereof.

BACKGROUND OF THE INVENTION

In the practice of surgery there currently exists a need for micro-fiber web structures with improved mechanical properties, such as higher elongation to break. These micro-fiber web materials can be used, for example, in both soft and hard tissue repair, to reinforce tissue structures, to separate tissues, to regenerate tissues, and to replace tissues. The micro-fiber webs can also be used as components of other device structures. Various devices have been produced from different polyhydroxyalkanoates (PHAs).

U.S. Pat. No. 8,034,270 to Martin et al. discloses monofilament and multifilament knitted meshes of P4HB produced by knitting monofilament and multifilament fibers of P4HB. WO 2011/119742 to Martin et al, discloses P4HB monofilament and multifilament fiber, coatings and spin finishes for these fibers, and medical devices made from P4HB monofilament and multifilament fibers. U.S. Pat. No. 8,016,883 to Coleman et al. discloses methods and devices for rotator cuff repair, including medical devices containing knitted meshes of P4HB and nonwovens made from P4HB multifilament fibers.

U.S. Pat. No. 8,287,909 to Martin et al. discloses medical devices containing melt-blown nonwovens of poly-4-hydroxybutyrate and copolymers thereof with average fiber diameters of 1 µm to 50 µm.

WO 2011/159784 to Cahil et al. discloses medical devices containing dry spun nonwovens of P4HB and copolymers thereof, and continuous processing methods for their preparation. The fibers of the nonwovens have average diameters in the micron range.

A low melting and high modulus electrospun scaffold made from a blend of P4HB and poly(ϵ-caprolactone) (80:20), and spun from a 7.5 wt./v-% THF solution, is disclosed by Vaz, et al., Novel Electrospun P4HB:PCL Scaffold for Aortic Valve Tissue Engineering, Poster Presentation (2004), Eindhoven University of Technology.

WO 95/23249 to Noda et al. discloses fabrics prepared from other polyhydroxyalkanoates, namely, poly-3-hydroxybutyrate (P3HB) and poly-3-hydroxybutyrate-co-3-hydroxyvalerate (PHBV) by dry spinning for use in non-medical applications such as disposable absorbent articles, including diapers, incontinence articles, and sanitary napkins.

A number of absorbable materials have been used to produce micro-fiber webs for use in surgery. For example, micro-fiber webs have been made from polyglycolic acid (PGA) or copolymers containing lactic acid. These materials do not, however, have ideal properties for many procedures and applications. For example, micro-fiber webs made from glycolic acid containing polymers have low elongation to break, degrade quickly, are moisture sensitive and release acidic degradation products that can cause inflammatory reactions.

It is therefore an object of the present invention to provide continuous processes for production of micro-fiber webs of P4HB and copolymers thereof, with improved physical and mechanical properties for medical applications.

It is an object of the present invention to provide methods to produce micro-fiber webs of absorbable P4HB and copolymers thereof by centrifugal spinning, wherein the fibers have average diameters ranging from 0.01 to 100 microns, a high degree of orientation in the fibers and high surface areas to volume ratios.

It is a further object of the present invention to provide methods to produce micro-fiber webs of absorbable P4HB and copolymers thereof without substantial loss of the polymer molecular weight during processing.

It is still a further object of the present invention to provide methods to produce micro-fiber webs of absorbable P4HB and copolymers thereof with a high degree of molecular orientation in the fibers.

It is yet another object of the present invention to provide methods to produce micro-fiber webs of absorbable P4HB and copolymers thereof wherein some or all of the fibers in the web are crimped.

It is still another object of the present invention to provide methods to produce micro-fiber webs of absorbable P4HB and copolymers thereof with improved mechanical properties.

It is another object of the present invention to provide continuous processes to produce medical devices containing micro-fiber webs of P4HB and copolymers without substantial loss of molecular weight during the spinning process.

SUMMARY OF THE INVENTION

Micro-fiber webs containing fibers of P4HB or co-polymers thereof, and methods for producing them, have been developed. The micro-fibers have average diameters ranging from 0.01 to 100 µm. Micro-fiber webs with higher elongation to break values can be made by centrifugal spinning. The micro-fiber webs contain crimped fibers, unlike fibers derived by melt-blown extrusion, dry spinning and electrospinning. The micro-fiber webs also have higher elongation to break values than nonwovens produced by melt-blown extrusion, dry spinning and electrospinning.

Also disclosed are methods for making micro-fiber webs from P4HB. The methods allow the micro-fiber webs to be produced without substantial loss of the polymer weight average molecular weight. The micro-fiber webs containing/including micro-fibers of poly-4-hydroxybutyrate or copolymer thereof, are preferably derived by centrifugal spinning. In one embodiment, the polymer or copolymer is dissolved in a solvent, the polymer solution is pumped through a rotating spinneret, and fibers are collected as a web. The equipment for centrifugal spinning typically includes one or more spinnerets incorporating one or more orifices, fed by a polymer melt or a solution of P4HB or copolymer thereof, which can be rotated at high speed. Rotation of a spinneret at high speed applies a centrifugal force to the polymer solution and causes it to be drawn from the orifice of the spinneret and released as a polymer jet. Evaporation of the solvent from the polymer jet results in the formation of fiber, and the fiber is collected to form a micro-fiber web. The average diameter of the fibers in the micro-fiber web ranges from 0.01 to 100 microns.

The properties of the fibers and micro-fiber webs may be tailored by varying certain parameters of the centrifugal spinning process. These include (i) equipment settings, such as spinneret configurations, orifice diameter, and distance between the spinneret and collector, (ii) operating conditions, such as the angular velocity, pressure, and temperature, and (iii) polymer solution properties, such as viscoelasticity, surface tension, viscosity, and solvent evaporation rate.

The micro-fiber webs produced by centrifugal spinning may be used as medical devices or components thereof. Applications of the medical devices include the repair, replacement or regeneration of soft and hard tissues, such as wound support, repair patches, tissue engineering scaffolds, tissue separation membranes, cardiovascular patches, wound dressings, and devices for plastic surgery.

BRIEF DESCRIPTION OF THE DRAWINGS

FIG. 1 is a diagram that illustrates an equipment set up used to manufacture micro-fiber webs from poly-4-hydroxybutyrate and copolymers thereof, by centrifugal spinning.

DETAILED DESCRIPTION OF THE INVENTION

I. Definitions

"Absorbable" as generally used herein means the material is broken down in the body and eventually eliminated from the body within five years.

"Aspect ratio" as used herein is defined as L/2r where L is the length of the spinneret, and r is the radius of the orifice of the spinneret.

"Bicomponent" as generally used herein means a micro-fiber web structure made of two or more materials.

"Biocompatible" as generally used herein means the biological response to the material or device being appropriate for the device's intended application in vivo. Any metabolites of these materials should also be biocompatible.

"Blend" as generally used herein means a physical combination of different polymers, as opposed to a copolymer formed two or more different monomers.

"Crimped fiber" as generally used herein means the fiber is wavy and not straight.

"Copolymers of poly-4-hydroxybutyrate" as generally used herein means any polymer of 4-hydroxybutyrate with one or more different hydroxy acid units.

"Draw ratio" as used herein means the ratio of the length of the drawn rod stock to that of the length of the undrawn profile.

"Implant" as generally used herein include medical devices that are used in vivo as well as those that contact the surface of the body or are inserted into any orifice of the body.

"Molecular weight" as used herein, unless otherwise specified, refers to the weight average molecular weight (Mw), not the number average molecular weight (Mn), and is measured by GPC relative to polystyrene.

"Elongation to break" as used herein means the increase in length of a material that occurs when tension is applied to break the material. It is expressed as a percentage of the material's original length.

"Micro-fibers" as generally used herein means fiber having average diameters ranging from 0.01 μm to 100 μm.

"Molecular weight" as used herein, unless otherwise specified, refers to the weight average molecular weight (Mw), not the number average molecular weight (Mn), and is measured by GPC relative to polystyrene.

"Poly-4-hydroxybutyrate" as generally used herein means a homopolymer of 4-hydroxybutyrate units. It may be referred to herein as P4HB or TephaFLEX® biomaterial (manufactured by Tepha, Inc., Lexington, Mass.).

"Resorbable" as generally used herein means the material is broken down in the body and eventually eliminated from the body. The terms "resorbable", "degradable", "erodible", and "absorbable" are used somewhat interchangeably in the literature in the field, with or without the prefix "bio". Herein, these terms will be used interchangeably to describe material broken down and gradually absorbed or eliminated by the body, whether degradation is due mainly to hydrolysis or mediated by metabolic processes.

"Web" as generally used herein means a structure formed by entangling fibers, and excludes webs formed by weaving or knitting.

II. Compositions

The compositions described herein are based on methods developed to produce medical devices containing micro-fiber webs of P4HB and copolymers thereof with high surface area to volume ratios.

A. Micro-Fiber Webs Made from P4HB and Copolymers Thereof.

Micro-fiber webs can be prepared by centrifugal spinning with high surface area to volume ratios. In a preferred embodiment, micro-fiber webs of P4HB and copolymers thereof are prepared by centrifugal spinning, wherein the fibers have average diameters ranging from 0.01 μm to 100 μm. The micro-fiber web of P4HB and copolymers thereof can have a thickness of from 0.05 mm to 5 mm.

It has been discovered that some or all of the fibers in the micro-fiber webs produced by centrifugal spinning can be crimped. In contrast, fibrous structures of P4HB and copolymers thereof produced by melt blowing, dry spinning, and electro spinning are straight and not crimped. Although not wishing to be bound by theory, the crimped fibers likely form because of the very high shear stress acting on the P4HB polymer or copolymer jet as it exits the spinneret orifice. Because of the viscoelastic nature of the P4HB polymers and copolymers, this very high shear stress places the fiber under significant tension, which is suddenly released when the next polymer jet is ejected, causing the fiber to relax and crimp. The presence and degree of crimping is dependent on the rotational speed of the spinneret(s).

The micro-fibers in the web made according to the methods disclosed herein are crimped, conferring superior mechanical properties on the web. The webs made with crimped fibers have higher elongation to break values and a higher orientation than those that are produced by melt blowing, dry spinning and electrospinning. In a particularly preferred embodiment, the micro-fiber webs have an elongation to break greater than 210%, which is higher than the elongation to break values of fibrous constructs of P4HB and copolymers thereof produced by melt-blowing, dry spinning and electrospinning.

The weight average molecular weight of the polymer or copolymer decreases less than 20% of its original value during centrifugal spinning, more preferably less than 15%, and even more preferably less than 10%. In some embodiments, the weight average molecular weight of the polymer may decrease less than 5% of its original value during centrifugal spinning, more preferably, less than 2% or its original value during centrifugal spinning. In contrast, thermal processing of the polymer and copolymer results in substantial loss of weight average molecular weight that exceeds 20%. The decrease in molecular weight loss during processing is a particular advantage when it is desirable to retain mass and/or mechanical properties, such as burst strength, in vivo, for a prolonged period of time, since lower molecular weight P4HB degrades faster in vivo than higher molecular weight P4HB.

In some embodiments, the micro-fibers may be crosslinked. The polymer may be coated with a crosslinking agent or derivatized using chemical agents or gas plasma to introduce new functional groups prior to cross-linking. Suitable crosslinking agents include, but are not limited to, bifunctional crosslinking agents reactive toward hydroxyl and/or carboxylic acid groups. Representative covalent crosslinking agents include carbodiimides and diisocyanates. In certain embodiments, the covalent crosslinking agent is selected from epichlorohydrin, gluteraldehyde, hexamethylene diisocyanate, adipic acid hydrazide, and 1-ethyl-3-(3-dimethylaminopropyl) carbodiimide hydrochloride. Crosslinking of the polymer may also be achieved through exposure to radiation such as gamma irradiation or ultraviolet light or generation of free radicals.

The centrifugally spun micro-fiber webs of P4HB and copolymers thereof provided herein are biocompatible and can be used in medical applications, for example, as implants such as devices for soft and hard tissue repair, replacement, and regeneration, temporary tissue support, tissue separation, as well as devices or components of devices for tissue in-growth (or guided tissue regeneration) and tissue engineering.

The polymers used to make the micro-fiber web can optionally include an additive, and/or be blended with another polymer.

i. P4HB Polymer and Co-Polymers

The micro-fiber webs are formed of poly-4-hydroxybutyrate (P4HB) or a copolymer thereof. Copolymers include 4-hydroxybutyrate copolymerized with another hydroxyacid, such as 3-hydroxybutyrate, and 4-hydroxybutyrate copolymerized with glycolic acid or lactic acid monomer. P4HB and copolymers thereof can be obtained from Tepha, Inc. of Lexington, Mass.

In a preferred embodiment, the P4HB homopolymer and copolymers thereof have a weight average molecular weight, Mw, within the range of 50 kDa to 1,200 kDa (by GPC relative to polystyrene) and more preferably from 100 kDa to 600 kDa. A weight average molecular weight of the polymer of 50 kDa or higher is preferred in order to improve the strength of the micro-fiber. The viscosity of the polymer solution may also be tailored by varying the molecular weight of the P4HB homopolymer and copolymers thereof (as well as varying the solvent system).

Poly-4-hydroxybutyrate (P4HB) and copolymers thereof can be produced using transgenic fermentation methods, see, for example, U.S. Pat. No. 6,548,569 to Williams et al., and are produced commercially, for example, by Tepha, Inc. (Lexington, Mass.). Poly-4-hydroxybutyrate (P4HB, Tepha-FLEX® biomaterial) is a strong, pliable thermoplastic polyester that, despite its biosynthetic route, has a relatively simple structure. Upon implantation, P4HB hydrolyzes to its monomer, and the monomer is metabolized via the Krebs cycle to carbon dioxide and water.

The polymer belongs to a larger class of materials called polyhydroxyalkanoates (PHAs) that are produced by numerous naturally occurring microorganisms or genetically engineered microorganisms (see, for example, Steinbüchel, et al., *FEMS Microbial. Lett.*, 128:219-228 (1995) and Agnew and Pfleger, *Chemical Engineering Science*, 103:58-67 (2013)). In nature these polyesters are produced as storage granules inside cells, and serve to regulate energy metabolism. They are also of commercial interest because of their thermoplastic properties, and relative ease of production using recombinant bacteria or plants. Chemical synthesis of P4HB has been attempted, but it has been impossible to produce the polymer with a sufficiently high molecular weight that is necessary for most applications (Hori, Y., et al., *Polymer* 36:4703-4705 (1995) and Houk, et al., *J Org. Chem.*, 73 (7):2674-2678) (2008).

U.S. Pat. Nos. 6,245,537, 6,623,748, 7,244,442, and 8,231,889 describe methods of making PHAs with little to no endotoxin, which are suitable for medical applications. U.S. Pat. Nos. 6,548,569, 6,838,493, 6,867,247, 7,268,205, 7,179,883, 7,268,205, 7,553,923, 7,618,448 and 7,641,825 and WO 2012/064526 describe use of PHAs to make medical devices. Copolymers of P4HB include 4-hydroxybutyrate copolymerized with 3-hydroxybutyrate or glycolic acid (U.S. Pat. No. 8,039,237 to Martin and Skraly, U.S. Pat. No. 6,316,262 to Huisman et al., and U.S. Pat. No. 6,323,010 to Skraly et al.). Methods to control molecular weight of PHA polymers have been disclosed by U.S. Pat. No. 5,811,272 to Snell et al.

PHAs with controlled degradation and degradation in vivo of less than one year are disclosed by U.S. Pat. Nos. 6,548,569, 6,610,764, 6,828,357, 6,867,248, and 6,878,758 to Williams et al. and WO 99/32536 to Martin et al. Applications of P4HB have been reviewed in Williams, S. F., et al., *Polyesters, III*, 4:91-127 (2002), Martin, et al., *Biochem. Eng. J.* 16:97-105 (2003), and by Williams, et al., *Biomed. Tech.* 58(5):439-452 (2013). Medical devices and applications of P4HB have also been disclosed by WO 00/56376 to Williams et al. Several patents including U.S. Pat. Nos. 6,555,123, 6,585,994, and 7,025,980 describe the use of PHAs in tissue repair and engineering.

P3HB and P4HB although differing only by the position of the hydroxyl group on the monomers, have substantially different thermal and physical properties than poly-4-hydroxybutyrate and copolymers thereof. For example, P3HB has a melting point and glass transition temperature of approx. 180° C. and 1° C., respectively, and an elongation to break of about 3%, whereas P4HB has a melting point of 60° C., a glass transition temperature of approx. −51° C., and elongation to break of around 1,000%. As such, P3HB is a brittle polymer that has properties resembling polystyrene whereas P4HB is a strong but extensible polymer similar to low-density polypropylene. Furthermore, P3HB and PHBV have also been reported to degrade very slowly in vivo with material still present after 24 months (Duvernoy, et al. A biodegradable patch used as a pericardial substitute after cardiac surgery: 6- and 24-month evaluation with CT, *Thorac. Cardiovasc. Surgeon*, 43:271-274 (1995)), and are therefore not well suited for many in vivo surgical applications.

ii. Polymer Blends and Additives

If desired, the PHA polymers may be blended or mixed with other materials prior to centrifugal spinning. In a particularly preferred embodiment, P4HB and its copolymers may be blended with other absorbable polymers. Examples of other absorbable polymers include, but are not limited to, polymers containing glycolic acid, lactic acid, 1,4-dioxanone, trimethylene carbonate, 3-hydroxybutyric acid, epsilon-caprolactone, and include polyglycolic acid, polyglycolide, polylactic acid, polylactide, polydioxanone, polycaprolactone, copolymers of glycolic and lactic acids such as VICRYL® polymer, and the MAXON® and MONOCRYL® polymers. The ratio of the PHA polymer in the blend to the non-PHA polymer component(s) may be varied in order to select the desired properties of the micro-fibers.

The P4HB homopolymer and copolymers thereof may also be blended with other synthetic polymers, such as polyethylene oxide, polypropylene oxide, polyoxyethylene-polypropylene oxide block copolymers ("PLURONICS®", BASF), as well as other components prior to centrifugal spinning. If desired, the P4HB homopolymer and copolymers thereof may also be blended with natural polymers, such as collagen, silk, proteins, polysaccharides, glycosaminoglycans, hyaluronic acid, heparin, and chitosan, as well as other components prior to centrifugal spinning.

In addition to blending the P4HB polymers and copolymers with other polymers, additives may also be added to the polymers and copolymers prior to centrifugal spinning Other additives include, but are not limited to, surfactants, plasticizers, nucleants, compatibilizes, porogens, dyes, and organic or inorganic powders including fillers and bioceramics. Particularly preferred bioceramics are degradable, and include tricalcium phosphate ($\alpha$ and $\beta$ forms of TCP— with a nominal composition of $Ca_3(PO_4)_2$), biphasic calcium phosphate (BCP), calcium sulfate, calcium carbonate, hydroxyapatite and other calcium phosphate salt-based bioceramics. Bio-active glasses may also be incorporated prior to centrifugal spinning. U.S. Pat. No. 6,905,987 to Noda et al. discloses examples of plasticizers that can be incorporated.

It may be advantageous to incorporate contrast agents, radiopaque markers, imaging agents, or radioactive substances into the polymer compositions prior to centrifugal spinning. Alternatively, these can be incorporated into the micro-fiber webs during subsequent processing steps.

It may also be advantageous to incorporate drugs, antibiotics, antibacterial agents, antiviral agents or antifungal agents into the polymer compositions prior to centrifugal spinning. Alternatively, these can be incorporated into the micro-fiber webs during subsequent processing steps.

B. Structures Containing Micro-Fiber Webs

The micro-fiber webs resulting from the centrifugal spinning process may be used in combination with other structural components. The structures may in addition to structural components, contain additional components such as therapeutic, diagnostic or prophylactic agents, wetting agents and surface coatings.

The centrifugally spun structures have properties that are substantially improved for many medical applications relative to glycolic and lactic acid derived fibrous structures. While structures derived from polymers of glycolic and lactic acids release acidic monomers, centrifugally spun structures derived from P4HB and copolymers thereof release much less acidic degradation products since the 4-hydroxybutyric acid monomer is less acidic (i.e. has a higher pKa) than that of glycolic and lactic acids. The centrifugally spun structures derived from P4HB and copolymers thereof will also retain strength longer in vivo due to the slower degradation of these polymers in vivo, and therefore the structures will retain their integrity for longer. This is important where healing requires a prolonged period, and is particularly important where the centrifugally spun structure is in the form of a scaffold for tissue engineering which needs to be present for an extended period to allow time for tissue ingrowth and tissue maturation.

i. Structural Components

The micro-fiber web may be combined or laminated with a nonwoven fabric, woven fabric, knitted mesh or film or form. Alternatively the centrifugally spun fibers can be deposited directly on another material by using it as the collecting plate. For example, a laminate or bicomponent material can be directly formed by depositing centrifugally spun micro-fibers of P4HB and copolymers thereof onto support structures such as a nonwoven fabric, woven fabric, knitted mesh, foam, or film. These other materials may be non-absorbable or may be absorbable.

In a particularly preferred embodiment, the micro-fibers are centrifugally spun onto a: P4HB monofilament mesh, a P4HB multifilament mesh, a P4HB nonwoven fabric, a P4HB woven fabric, a P4HB foam, or a P4HB film, and any combinations thereof. In an even more preferred embodiment, the centrifugally spun micro-fibers cover more than 10% of the surface area of the P4HB monofilament mesh, a P4HB multifilament mesh, a P4HB nonwoven fabric, a P4HB woven fabric, a P4HB foam, or a P4HB film, and any combinations thereof.

In another embodiment, bicomponent structures may be prepared by centrifugally spinning P4HB or copolymer thereof with one or more different materials simultaneously from either the same solution or from different solutions using the same or different spinnerets.

Three-dimensional structures containing centrifugally spun micro-fibers of P4HB and copolymers thereof, may also be formed by using spinnerets that in addition to rotating are also moving, and by using moving collector plates, including other moving structural shapes used as collector plates.

The structures containing micro-fiber webs of P4HB and copolymers thereof may be subjected to further modification. These include heat treatments, pressure treatment, compression, cutting, calendaring, bonding, piercing, laser cutting, laser drilling, air entanglement, water entanglement, chemical treatments, surface treatments, and or gas plasma treatments.

A significant advantage of using centrifugal spinning instead of melt blowing to produce webs of micro-fibers of P4HB and copolymers thereof is that the process can be controlled to allow the formation of webs with unexpectedly high cohesion of the fibers. This is achieved by controlling the solvent evaporation rate in order to collect fibers that briefly remain tacky thereby improving the fusion of the micro-fibers at their crossover points. The higher cohesion of the fibers, preferably combined with micro-fibers having higher degrees of orientation, results in webs with improved mechanical properties, such as burst strength and elongation to break.

ii. Other Components

The structures may in addition to structural components, contain additional components which are not structural. These other components may either be incorporated at the time of centrifugal spinning or after the centrifugal spinning process.

a. Therapeutic, Diagnostic or Prophylactic Agents

Bioactive agents which may be included into the micro-fiber webs disclosed herein include biologically, physiologically, or pharmacologically active substances that act locally or systemically in the human or animal body. Examples can include, but are not limited to, inorganic or organic synthetic molecules, anesthetics, hormones, small-molecule drugs, anti-inflammatory agents, immunomodulatory agents, molecules that promote cell migration, molecules that promote or retard cell division, molecules that promote or retard cell proliferation and differentiation, molecules that stimulate phenotypic modification of cells, molecules that promote or retard angiogenesis, molecules that promote or retard vascularization, molecules that promote or retard extracellular matrix disposition, molecules that promote wound healing, molecules that promote blood clotting, signaling ligands, platelet rich plasma, peptides, proteins, antibodies, growth factors, fibronectin, laminin, vitronectin, integrins, antibiotics, steroids, hydroxyapatite, silver particles, vitamins, non-steroidal anti-inflammatory drugs, glycoproteins, heparin, chitosan and derivatives thereof, alginate and derivatives thereof, collagen, sugars, polysaccharides, nucleotides, oligonucleotides, lipids, hyaluronic acid and derivatives thereof, allograft material, xenograft material, antisense molecules, aptamers, siRNA, nucleic acids, and combinations thereof.

Bioactive agents may also include compounds or materials intended to prevent infection such as antibiotics, antibacterials, antivirals and antifungals.

The structures containing micro-fiber webs may also be seeded with cells to improve tissue ingrowth and healing. In a particularly preferred embodiment, the structures contain signaling ligands, including members of the TGF-beta family, bone morphogenic proteins, fibroblast growth factors-1 and -2, plateletderived growth factor-AA and -BB, and platelet rich plasma and vascular endothelial cell-derived growth factor.

In yet another preferred embodiment the structures containing micro-fiber webs may be used for the controlled release of drugs, or incorporate systems for the controlled release of drugs.

b. Wetting Agents

Wetting agents designed to improve the wettability of the surfaces of the structures containing the micro-fiber webs may also be incorporated in order to allow fluids to be easily adsorbed onto the surfaces of the implant, device or dressing, and to promote cell attachment. Examples of wetting agents include polymers of ethylene oxide and propylene oxide, such as polyethylene oxide, polypropylene oxide, or copolymers of these, such as pluronics. Surfactants and emulsifiers may also be used as wetting agents. A coating may also be applied that is intended to reduce the rate of water vapor transmission. When used on a wound dressing, such coatings may help to retain moisture at the wound site and promote healing.

c. Surface Coatings

If desired, the structures containing the micro-fiber webs may be coated with a ceramic, preferably a resorbable ceramic. Resorbable bioceramics that can be used with the structures disclosed herein must: (i) be biocompatible, (ii) eventually be resorbed by the body, and (iii) permit the replacement or repair of damaged tissues in the body. Examples of resorbable bioceramics include tricalcium phosphate ($\alpha$ and $\beta$ forms of TCP—with a nominal composition of $Ca_3(PO_4)_2$), biphasic calcium phosphate (BCP), calcium sulfate, hydroxylapatite, calcium carbonate, and other calcium phosphate salt based bioceramics. Bio-active glasses may also be incorporated into the structures containing micro-fiber webs. Bioactive glasses are composed of $SiO_2$, $Na_2O$, $CaO$ and $P_2O_5$ in specific proportions.

C. Formation into Devices

The centrifugally spun micro-fiber webs may be used to prepare structures that are suitable for use as medical devices. In particular, structures can be formed for use as implantable medical devices. For example, the structures containing micro-fiber webs made from P4HB and copolymers thereof may be used to make partially or fully absorbable biocompatible medical devices, or components thereof. Such devices include, but are not limited to, stent, stent graft, drug delivery device, device for temporary wound or tissue support, device for soft or hard tissue repair or regeneration, repair patch, tissue engineering scaffolds, retention membranes (for example, to retain bone graft), anti-adhesion membrane, tissue separation membrane, surgical textiles (including devices for face lift, neck lift, eyebrow lift, breast lift, or breast reconstruction), hernia repair device, hernia plug, cardiovascular patch, vascular closure device, sling, rotator cuff repair device, meniscus repair device, guided tissue repair/regeneration device, articular cartilage repair device, osteochondral repair device, bone void filler, nerve guide, tendon repair device, intracardiac septal defect repair device, including but not limited to atrial septal defect repair devices and patent foramen ovale (PFO) closure devices, left atrial appendage (LAA) closure device, pericardial patch, bulking and filling agent, vein valve, heart valve, bone marrow scaffold, meniscus regeneration device, ligament and tendon graft, spinal fusion device, skin substitute, wound healing device, dural substitute, bone graft substitute, wound dressing, ulcer repair device, and a hemostat.

The centrifugally spun micro-fiber webs may be used to prepare structures that are suitable for use as wound dressings. In particular, structures can be formed for use as external medical devices. These may include dressings containing alginates, dressings for allergy-induced wounds, dressings for amputation surgery, dressings for burn wound care, dressings for diabetic foot ulcers, dressings for chronic wounds, dressings for deep wounds, dressings for diabetes wounds, dressings for diabetic ulcers diabetic wound care diabetic wounds, dressings for infected wounds, dressings for pressure ulcers, dressings for vascular wounds, dressings for venous stasis wound care, dressings for drainage wounds and dressings for wound healing.

III. Methods of Manufacturing Micro-Fiber Webs of P4HB and Copolymers Thereof and Three Dimensional Structures Methods are provided for manufacturing micro-fiber webs of P4HB and copolymers thereof, as well as three-dimensional structures containing the micro-fibers, by centrifugal spinning.

A major advantage of the method over other processing methods, such as melt blowing, dry spinning and electrospinning is that some or all of the micro-fibers in the web can be crimped. In contrast, fibers produced by melt blowing, dry spinning and electrospinning are straight and not crimped.

Another advantage of the micro-fiber webs produced by centrifugal spinning compared to fiber based products produced by melt processing is that the weight average molecular weight of the polymer or copolymer may decrease less than 20% of its original value during centrifugal spinning, more preferably less than 15%, and even more preferably less than 10%. In some embodiments, the weight average molecular weight of the polymer may decrease less than 5% of its original value during centrifugal spinning, more preferably, less than 2% or its original value during centrifugal spinning. In contrast thermal processing of the polymer and copolymer results in substantial loss of weight average molecular weight that exceeds 20%. WO 09/085823 to Ho et al., for example, describes methods to produce melt blown fibers of P4HB and copolymers thereof by melt processing wherein the polymer loses 47-52% of the polymer's initial molecular weight.

A further advantage of the method over melt processing methods is the higher degree of orientation of the centrifugally spun micro-fibers. By increasing the distance between the orifice and the collector (for a given spinneret angular velocity) it is possible to increase the orientation of the fiber as well as decrease the diameter of the fiber. In contrast, melt-blown fibers are not substantially oriented prior to collection. The higher degree of orientation is thought to be due to the continued stretching of the fiber as it orbits the spinneret before it reaches the collector. During the orbiting of the spinneret, the diameter of the fiber is reduced, and the fiber continues to be stretched. While not wishing to be bound by theory, the continued stretching of the fiber results in molecular orientation of the polymer. Since it is known that increased molecular orientation results in increased tensile strength of fibers of P4HB and copolymers thereof (Martin, et al., *Biochem. Eng. J.* 16:97-105 (2003)), centrifugal spinning of P4HB and copolymers thereof produces fibers with higher tensile strength than, for example, dry spinning. Higher tensile strength micro-fibers of P4HB and copolymers thereof is important in medical applications where not only high initial strength is required at the time of implantation, but also when prolonged strength retention is necessary since a higher degree of orientation slows polymer degradation in vivo and improves strength retention. (Williams, et al. *Biomed Tech (Berl).*, 58(5):439-52 (2013)). For example, prolonged strength retention is important in the reinforcement of repaired tissues.

An additional advantage of the method over electrospinning is a substantially improved yield. Electrospinning uses electrostatic forces to draw fibers, which can be a very slow process, whereas centrifugal spinning uses centrifugal forces to throw or sling fibers from the orifice of the spinneret. In the laboratory a ten-fold increase in yield for centrifugal spinning over electrospinning can be readily achieved as the polymer solution can be ejected from the orifice(s) of the spinneret at a much higher production rate. (For example, a laboratory electrospinning machine may run at a rate of 0.1 gram/hour polymer, whereas a laboratory centrifugal spinning machine may easily run at a rate of 1.0 gram or more/hour polymer per orifice.)

A. Method of Making P4HB Polymer or Copolymer Micro-Fiber Webs by Centrifugal Spinning The micro-fiber webs of P4HB polymer or copolymer are prepared using centrifugal spinning. A suitable centrifugal spinning apparatus is shown in FIG. 1, and consists of at least one spinneret fed by the polymer solution. (The spinneret may be fed by a reservoir, or using a precision pump, and may contain one or more orifices.). Typically, the collector is circular or cylindrical such that the distance between the spinneret and the collector is constant. The collector may be, for example, a circle of vertical prongs, a continuous substrate, or potentially a substrate for coating with a micro-fiber web. However, the collector does not need to be cylindrical or circular. The centrifugal spinning equipment is designed so that the spinneret can be rotated at high speed.

In a preferred method, micro-fiber webs of P4HB polymer or copolymer thereof may be prepared by: (a) preparing a spinning solution of the poly-4-hydroxybutyrate or copolymer thereof by dissolving the polymer or copolymer in an organic solvent; (b) optionally adding an additive to the spinning solution; (c) spinning the solution using a centrifugal spinner. The spinning solution or solutions are ejected from one or more spinnerets through a single orifice or a plurality of orifices. In some embodiments, the micro-fiber web is produced by simultaneously spinning the micro-fiber web comprising poly-4-hydroxybutyrate or copolymer with a second material or as a blend with a second material. The microfiber web may be further coated with a radiolabelled substance, imaging agent, radiopaque marker, contrast agent, dye, and bioactive agent.

There are no particular restrictions on the solvent that can be used to make the polymer solution except it must be capable of dissolving the P4HB and copolymers thereof, and evaporate during the spinning stage to allow the formation of the centrifugally spun micro-fibers. The rate of evaporation should be fast enough that fibers are collected and not a film, and slow enough to allow for elongation of the fiber. If the rate of evaporation is too high then the elongation of the fiber will be disturbed and larger diameter fibers than desired may be produced.

Volatile solvents that are liquid at room temperature, and have boiling points no higher than 200° C. are particularly preferred. Examples of volatile solvents include methylene chloride, chloroform, dichloroethane, tetrachloroethane, trichloroethane, dibromomethane, bromoform, acetone, acetonitrile, tetrahydrofuran, 1,4-dioxane, 1,1,1,3,3,3-hexafluoroisopropanol, toluene, xylene, dimethylformamide (DMF), dimethylacetamide (DMA), N-methylpyrrolidone, and dimethylsulfoxide. These solvents may be used alone, or two or more solvents may be combined for use as a mixed solvent system. Particularly preferred solvents include polar organic solvents such as methylene chloride, chloroform, dichloroethane, tetrachloroethane, trichloroethane, dibromomethane, bromoform, tetrahydrofuran, acetone, dimethylformamide, and 1,4-dioxane. Additionally, the mixed solvent system may include liquids that do not dissolve the polymer, but rather are considered non-solvents for the polymer, such as water or methanol. These non-solvents may be chosen to alter the solvent evaporation rate, viscosity, polymer solubility or other spinning parameters. These non-solvents for the polymer may be chosen as solvents for other potential additives that would otherwise not be soluble in the spinning solution, such as proteins, drugs, glycosaminoglycans, or other additives.

In a preferred embodiment, micro-fibers of P4HB and copolymers thereof are prepared from solutions with polymer concentrations preferably from 1 to 30 wt %, more preferably 2 to 25 wt %, and even more preferably 3 to 15 wt %. If necessary, temperatures ranging from 0-100° C. may be selected in order to further control the evaporation rate of the solvent. The spinneret may be heated or cooled in order to provide the desired evaporation temperature for the formation of micro-fibers. The temperature or airflow within the collection chamber may also be altered to control the solvent evaporation rate.

A collector is positioned at a desired distance from the spinneret in order to collect the micro-fibers, and allow the formation of a micro-fiber web. As the spinneret is rotated at high speed, the polymer solution is subject to a centrifugal force that causes it to be drawn from the orifice(s) of the spinneret and released as a polymer jet. Micro-fibers form from the polymer jet as the solvent evaporates, and can be collected in the form of a micro-fiber web at the collector. Prior to reaching the collector, the micro-fiber may or may not always travel directly outwards to the collector.

For low viscosity polymer solutions, the micro-fiber will have a greater tendency to travel continuously outward to the collector. However, for higher viscosity polymer solutions and at increased angular velocity, the micro-fiber may initially travel outwards, but then be pulled inwards before traveling outwards again to the collector. The trajectory of the micro-fiber starting at the spinneret may loop around the rotating spinneret several times in a spiral manner before it is collected. The number of times the micro-fiber orbits the spinneret will depend in part on the angular velocity of the spinneret, the composition of the polymer solution, and the operating conditions. In general the more times the micro-fiber orbits the spinneret, the longer it will become, and at the same time the diameter of the micro-fiber will decrease. The average diameter of the fiber can therefore be controlled not only by the orifice diameter, but also by controlling the angular velocity and viscosity of the polymer solution.

A number of parameters can be varied to control the sizes of the micro-fibers. These include, but are not limited to, (i) equipment settings, such as spinneret configurations (including nozzle direction), orifice diameter, and distance between the spinneret and collector, (ii) operating conditions, such as the angular velocity, flow rate, humidity, pressure and temperature, and (iii) polymer solution properties, such as choice of solvent, polymer concentration, viscoelasticity, surface tension, viscosity, and solvent evaporation rate.

At lower rotational speeds of the spinneret, the micro-fibers have larger average diameters. These diameters decrease as the angular velocity is increased. The diameters of the micro-fibers also generally decrease with increasing viscosity. The degree of crimping of the fibers is also dependent upon the angular velocity. At low rotational speeds little, if any, crimping of the micro-fibers is observed. However, at higher rotational speeds (for example above 4,000 rpm) the fibers become increasingly more crimped. In a preferred embodiment, micro-fibers of P4HB and copolymers thereof are prepared at a rotational speed between 500 and 25,000 rpm, and more preferably from 1,000 to 10,000 rpm.

As well as controlling the viscosity of the polymer solution by judicious choice of solvent and concentration, the viscosity of the polymer solution may also be altered by using P4HB polymers and copolymers thereof of different molecular weights. In some embodiments, the molecular weight of the polymer is between 50 kDa and 1,200 kDa, and in a preferred embodiment the polymer molecular weight is between 100 kDa and 600 kDa.

The distance between the spinneret and the collector may be adjusted to form the required micro-fibers. If the collector is placed too close to the spinneret it is likely that fibers will not be formed and the polymer will just be uniformly collected. Or the fibers collected will not be fully stretched.

In addition to producing micro-fibers of different average diameter by altering the viscosity (i.e. concentration) of the polymer solution, feed rate (e.g. by applying increased pressure to the polymer solution) and angular velocity, it is also possible to control the diameter of the micro-fibers by changing the orientation of the orifice(s). The orifice may be oriented so that the polymer jet is released in: (i) the direction of rotation of the spinneret, (ii) the direction opposite to the direction of rotation, or (iii) a direction straight ahead such that it is neither in the direction or opposite to the direction of rotation.

Small changes in the average diameter of the micro-fibers may also be obtained by changing the dimensions of the orifice. For example, varying the length of the spinneret or radius of the orifice will change the aspect ratio, and yield micro-fibers with different average diameters. The diameter of the orifice(s) may be from 5 µm to 5 mm, and more preferably from 100 µm to 1 mm.

B. Method of Making P4HB Polymer or Copolymer Structures Containing Other Micro-Fibers and Bioactive Agents, by Centrifugal Spinning A particular advantage of the centrifugal spinning method is that the P4HB polymer or copolymer micro-fibers can be spun directly with bioactive agents and other additives. They may also be spun directly as blends with other polymers, or spun simultaneously with other polymer solutions to form micro-fiber webs containing micro-fibers of two or more different materials.

In an embodiment, P4HB or copolymer thereof may be dissolved in a solvent with a bioactive agent, and spun to form micro-fibers containing the bioactive agent. If the bioactive agent is not soluble in the solvent, then the bioactive agent may be dissolved in a solvent for the bioactive agent, mixed with the polymer solution to form a mixed solvent system or an emulsion, and the mixture centrifugally spun to form micro-fibers containing the bioactive agent.

In some embodiments, P4HB or copolymer thereof may be dissolved with another polymer in a solvent, and centrifugally spun to form a micro-fiber containing a blend of P4HB or copolymer thereof with another polymer. If the polymers are not soluble in the same solvent, then the polymers may be dissolved in different solvents, the polymer solutions combined, and micro-fibers centrifugally spun.

P4HB or copolymer thereof may also be centrifugally spun simultaneously with one or more different polymers to form a micro-fiber web containing two or more different types of fibers. For example, a centrifugal spinning apparatus with a spinneret containing two or more orifices, or two different spinnerets, may be set up such that at least one orifice is fed with a polymer solution of P4HB or copolymer thereof, and at least a second orifice is fed with a polymer solution of, for example, a protein such as collagen or silk in aqueous solution, or a polysaccharide such as chitosan in aqueous solution.

In yet a further embodiment, porous micro-fibers of P4HB and copolymers thereof can be produced by centrifugal spinning of mixtures of P4HB and copolymers thereof include a solvent and a non-solvent for P4HB or copolymer thereof. For example, a mixture or an emulsion containing P4HB, chloroform (as solvent) and glycerol (as non-solvent) may be centrifugally spun to form micro-fibers containing residual glycerol. The glycerol may be subsequently removed from the micro-fiber to yield a porous micro-fiber. In still a further embodiment, the non-solvent can be used to incorporate a bioactive agent or other additive in the fiber, and then be removed from the micro-fiber by vacuum drying or leaching to leave the bioactive agent or additive in the micro-fiber of P4HB or copolymer thereof.

We claim:

1. A micro-fiber web comprising fibers of poly-4-hydroxybutyrate or copolymer thereof, produced by centrifugal spinning, wherein the micro-fiber web has an elongation to break greater than 210%.

2. The micro-fiber web of claim 1 wherein some or all of the fibers are crimped.

3. The micro-fiber web of claim 1 wherein the weight average molecular weight of the poly-4-hydroxybutyrate or copolymer thereof is greater than 50 kDa relative to polystyrene.

4. The micro-fiber web of claim 1 further comprising fibers of a second material or comprising fibers of a blend of poly-4-hydroxybutyrate or copolymer thereof with a second material.

5. The micro-fiber web of claim 4 wherein the second material consists of proteins, polysaccharides, synthetic polymers, or polymers derived from glycolic acid, glycolid, lactic acid, lactide, 1,4-dioxanone, trimethylene carbonate and caprolactone.

6. The micro-fiber webs of claim 1 wherein the average diameter of the fibers is between 0.01 to 100 microns.

7. The micro-fiber webs of claim 1 wherein the centrifugal spun fibers have been deposited on a P4HB monofilament mesh, a P4HB multifilament mesh, a P4HB nonwoven fabric, a P4HB woven fabric, a P4HB foam, or a P4HB film.

8. The micro-fiber webs of claim 1 further comprising an additive wherein the additives are plasticizers, nucleants, compatibilizers, porogens, radiolabelled substances, imaging agents, radiopaque markers, contrast agents, dyes, and bioactive agents.

9. The micro-fiber webs of claim 7 wherein the micro-fiber web is formed into a medical device.

10. The micro-fiber webs of claim 9 wherein the micro-fiber web is formed into a wound dressing.

11. The device of claim 9 wherein the device is used for the repair, regeneration, remodeling or replacement of soft or hard tissue.

12. The device of claim 11 selected from the group consisting of a stent, stent graft, drug delivery device, device for temporary wound or tissue support, repair patch, tissue engineering scaffold, retention membrane, anti-adhesion membrane, tissue separation membrane, hernia repair device, hernia plug, cardiovascular patch, vascular closure device, sling, rotator cuff repair device, meniscus repair device, guided tissue repair/regeneration device, articular cartilage repair device, osteochondral repair device, bone void filler, nerve guide, tendon repair device, intracardiac septal defect repair device, atrial septal defect repair device, patent foramen ovale (PFO) closure device, left atrial appendage (LAA) closure device, pericardial patch, bulking and filling agent, vein valve, heart valve, bone marrow scaffold, meniscus regeneration device, ligament and tendon graft, spinal fusion device, skin substitute, wound healing device, dural substitute, bone graft substitute, wound dressing, ulcer repair device, a hemostat and devices selected from the group consisting of textiles for face lift, neck lift, eyebrow lift, breast lift and breast reconstruction.

13. A method for preparing micro-fiber webs of claim 1 by centrifugal spinning, wherein the method comprises:
(a) preparing a spinning solution comprising poly-4-hydroxybutyrate or copolymer thereof by dissolving the polymer or copolymer in an organic solvent;
(b) optionally adding an additive to the spinning solution;
(c) spinning the solution using a centrifugal spinner.

14. The method of claim 13 wherein the micro-fiber web is produced by simultaneously spinning the micro-fiber web comprising poly-4-hydroxybutyrate or copolymer with a second material or as a blend with a second material.

15. The method of claim 13 further comprising coating the micro-fiber web with a radiolabelled substance, imaging agent, radiopaque marker, contrast agent, dye, and bioactive agent.

16. The method of claim 13 wherein the solvent is selected from the group consisting of methylene chloride, chloroform, dichloroethane, tetrachloroethane, trichloroethane, dibromomethane, bromoform, tetrahydrofuran, acetone, acetonitrile, N-methylpyrrolidone, dimethylformamide, dimethylacetamide, dimethylsulfoxide, and 1,4-dioxane, alone, or combined into a mixed solvent.

17. The method of claim 13 wherein the spinning solution or solutions are ejected from one or more spinnerets through a single orifice or a plurality of orifices.

18. The methods of claim 13 wherein the micro-fiber web is formed into a device, and wherein the device is selected from the group consisting of a stent, stent graft, drug delivery device, device for temporary wound or tissue support, device for soft or hard tissue repair or regeneration, repair patch, tissue engineering scaffolds, retention membranes anti-adhesion membrane, tissue separation, membrane, hernia repair device, hernia plug, cardiovascular patch, vascular closure device, sling, rotator cuff repair device, meniscus repair device, guided tissue repair/regeneration device, articular cartilage repair device, osteochondral repair device, bone void filler, nerve guide, tendon repair device, intracardiac septal defect repair device, atrial septal defect repair devices, patent foramen ovale (PFO) closure devices, left atrial appendage (LAA) closure device, pericardial patch, bulking and filling agent, vein valve, heart valve, bone marrow scaffold, meniscus regeneration device, ligament and tendon graft, spinal fusion device, skin substitute, wound healing device, dural substitute, bone graft substitute, wound dressing, ulcer repair device, a hemostat and devices selected from the group consisting of textiles for face lift, neck lift, eyebrow lift, breast lift and breast reconstruction.

19. A method of using the device of claim 9 wherein the device is implanted in the body or applied topically to the surface of the body.

* * * * *